(12) United States Patent
Turner et al.

(10) Patent No.: US 8,948,879 B2
(45) Date of Patent: Feb. 3, 2015

(54) SELF-DIRECTING, TRANSCUTANEOUS STIMULATION ELECTRODE

(71) Applicant: Neuro Resource Group, Inc., Plano, TX (US)

(72) Inventors: David O. Turner, Royce City, TX (US); Paul J. Magee, Kings Langley (GB); Gary L. Byars, Richardson, TX (US); Charles H. Payne, Frisco, TX (US)

(73) Assignee: Neuro Resource Group, Inc., Plano, TX (US)

( * ) Notice: Subject to any disclaimer, the term of this patent is extended or adjusted under 35 U.S.C. 154(b) by 162 days.

(21) Appl. No.: 13/656,282

(22) Filed: Oct. 19, 2012

(65) Prior Publication Data

US 2013/0103129 A1    Apr. 25, 2013

Related U.S. Application Data

(60) Provisional application No. 61/627,839, filed on Oct. 19, 2011.

(51) Int. Cl.
*A61N 1/04* (2006.01)

(52) U.S. Cl.
CPC ............ *A61N 1/0488* (2013.01); *A61N 1/0476* (2013.01); *A61N 1/0492* (2013.01); *A61N 1/0456* (2013.01)

USPC .......................................... 607/115; 607/152

(58) Field of Classification Search
None
See application file for complete search history.

(56) References Cited

U.S. PATENT DOCUMENTS

| | | | | |
|---|---|---|---|---|
| 4,509,535 | A * | 4/1985 | Bryan | 607/152 |
| 4,969,463 | A * | 11/1990 | Dahl et al. | 607/5 |
| 5,002,527 | A * | 3/1991 | Reller et al. | 604/20 |
| 5,360,442 | A * | 11/1994 | Dahl et al. | 607/129 |
| 5,649,970 | A * | 7/1997 | Loeb et al. | 607/57 |
| 6,662,044 | B2 * | 12/2003 | Crawford et al. | 604/20 |
| 7,212,867 | B2 * | 5/2007 | Van Venrooij et al. | 607/116 |
| 7,221,981 | B2 * | 5/2007 | Gliner | 607/116 |

* cited by examiner

*Primary Examiner* — Kennedy Schaetzle
(74) *Attorney, Agent, or Firm* — Brown Fox Kizzia & Johnson PLLC

(57) ABSTRACT

A neurostimulation device is provided. The device has first and second physical electrode elements that cooperate to provide a plurality of virtual electrode pairs. The spacing between the physical elements, as well as the relative surface areas between the respective portions comprising the virtual pairs, is controlled to provide self-selecting and/or self-directing treatment capabilities.

22 Claims, 6 Drawing Sheets

SELF-DIRECTING, TRANSCUTANEOUS STIMULATION ELECTRODE

RELATED APPLICATIONS AND CLAIM FOR PRIORITY

This application claims the benefit of earlier filed provisional patent application Ser. No. 61/627,839 filed Oct. 19, 2011.

TECHNICAL FIELD

The disclosure relates generally to transcutaneous neurostimulation and, more particularly, to a self-directing electrode apparatus for effecting transcutaneous neurostimulation.

BACKGROUND

An objective of transcutaneous neurostimulation is to focus an adequate electrical energy concentration at a relatively small, preferred treatment location on the skin. The preferred treatment locations are typically locations such as nerve branches, trigger points, and acupuncture points, and are evidenced as points of lower relative impedance.

One approach to determine the location of low relative impedance points is to use an array of electrodes where the pairs of alternating polarity are individually addressable. This method is employed by Bijelic in U.S. Patent Application Serial No. 2008/0027507. An operator can then step through the combinations of electrodes, scanning for low relative impedance values. After the low impedance points are identified, the operator must use another device to treat the identified areas. The process of scanning and treating must be repeated to accomplish the desired results. Performing this approach, either manually or in an automated fashion, is time-consuming and costly.

Other prior devices and methods do not address the problem. For example, in U.S. Pat. No. 4,238,726, Ichijo discusses a method of determining points of low impedance electrically without mentioning using an electrode configuration as a means. Molina-Negro et al., in U.S. Pat. No. 4,541,432, discuss using a waveform to treat pain without regard to the electrode configuration. Matos, in U.S. Patent Application Serial No. 2003/0233129, discusses a method of scanning and stimulating without regard to relative electrode size and spacing.

Another common method of locating low impedance points is to use a configuration of concentric electrodes. An outer electrode has a substantially larger area than a smaller, inner "treatment" electrode. The area ratio of the outer electrode to the inner electrode is typically between 1.2/1 and 5.0/1, and the spacing between the electrodes is controlled at a small dimension, which is typically less than 0.40 inches.

By measuring and noting the impedance measurements between the inner and outer electrodes, as the electrode pair is moved over the body, one can locate points of low impedance and, thus, preferred treatment locations. This is discussed generally by Colthurst in U.S. Pat. No. 7,483,734.

Axelgaard, in U.S. Pat. No. 6,038,485, discusses controlling current distribution and directing electrical pulses via rows and columns of electrodes. Axelgaard addresses spacing and area of individual electrodes but does not disclose anything but equal spacing and equal electrode areas. Schumann, in U.S. Patent Application Serial No. 2007/0106342, discusses a means of scanning and locating trigger points and mentions a relationship between spacing and skin conductance. However, Schumann does not teach anything about having different areas of electrodes in combination with particular spacing between the electrodes. Schumann also discusses "chasing the pain" via multiple cycles of scanning and treating. Also worth noting is that Bijelic, in U.S. Patent Application Serial No. 2008/0027507, discusses arrays of electrodes with a single spacing and single dimension.

SUMMARY

In connection with certain embodiment described herein, it has been recognized that there are two major drawbacks to prior approaches of locating low impedance points and treating those locations. First, the prior approaches do not allow for treating relatively larger areas. Typically, the prior approaches require multiple treatment locations for clinical effectiveness. Prior approaches also require a skilled therapist to scan the body by either sliding the electrode pair over the skin to locate treatment points, or use of a scanning machine (e.g., such as in the Bijelic reference). Either process is time-consuming and expensive. Second, the prior approaches do not provide unattended therapy. Thus, a skilled therapist is required for either scanning or treatment, and this is time-consuming and expensive. These drawbacks essentially make these prior methods cost-prohibitive for all but the most complex clinical conditions. Various embodiments of the present disclosure perform the locating and treatment processes automatically, without complex electronics or software.

In one example, an apparatus is provided for neurostimulation. The apparatus includes a first physical electrode element having a first polarity and a second continuous physical electrode element having a second polarity different from the first polarity. The first and second physical electrode elements cooperate to form a plurality of virtual electrode pairs. Each pair has a first electrode part and a second electrode part. The first electrode part is a portion of the first physical electrode element and the second electrode part is a portion of the second physical electrode element.

According to one alternative aspect, at least one of the first electrode parts includes an arm. At least one of the second electrode parts includes a C-shaped portion of the first physical electrode element. The C-shaped portion at least partially surrounds the arm.

According to another alternative aspect, at least one of the first electrode parts includes T-shaped portion. The T-shaped portion includes an arm and a pad extending from the arm. At least one of the second electrode parts comprises a C-shaped portion of the first physical electrode element and the C-shaped portion at least partially surrounds the T-shaped portion.

According to another alternative aspect, the second physical electrode element includes a longitudinal element and at least two transverse elements crossing the longitudinal element to form at least two cross structures. Each of the cross structures includes at least two of the arms of the plurality of virtual electrode pairs.

According to an alternative embodiment, the first physical electrode element includes a first base portion from which extend a plurality of first arms, and the second physical electrode element includes a second base portion from which extend a plurality of second arms. The first and second arms are interleaved and opposed to form a plurality of virtual electrode pairs.

According to another alternative embodiment, the second physical electrode element comprises a serpentine element having a plurality of transverse arms. At least one of the transverse arms of the serpentine element includes an arm of at least one of the virtual electrode pairs.

One or more of the embodiments may provide some, none, or all of certain of the following advantages. According to one advantage, only two electrical connections are required to provide equivalence to a multiplicity of electrode pairs. According to another advantage, the exact location of the ideal treatment point is not required, since the stimulation current is directed preferentially to low impedance tissue. According to yet another advantage, a moderately large area can be treated at once. According to yet another advantage, the electrode device is flexible, adheres to the patient's skin using adhesive, but may be removed and re-applied multiple times. According to yet another advantage, the small spacing of conductive pathways promotes improved therapeutic outcomes by avoiding painful muscle contractions.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

Among other things, various embodiments provide electrode configurations for transcutaneous neurostimulation. The electrode configurations may be incorporated into a self-directing electrode apparatus for effecting transcutaneous neurostimulation. The electrode configurations may enable locating low impedance points and treating those locations.

Figure 1:
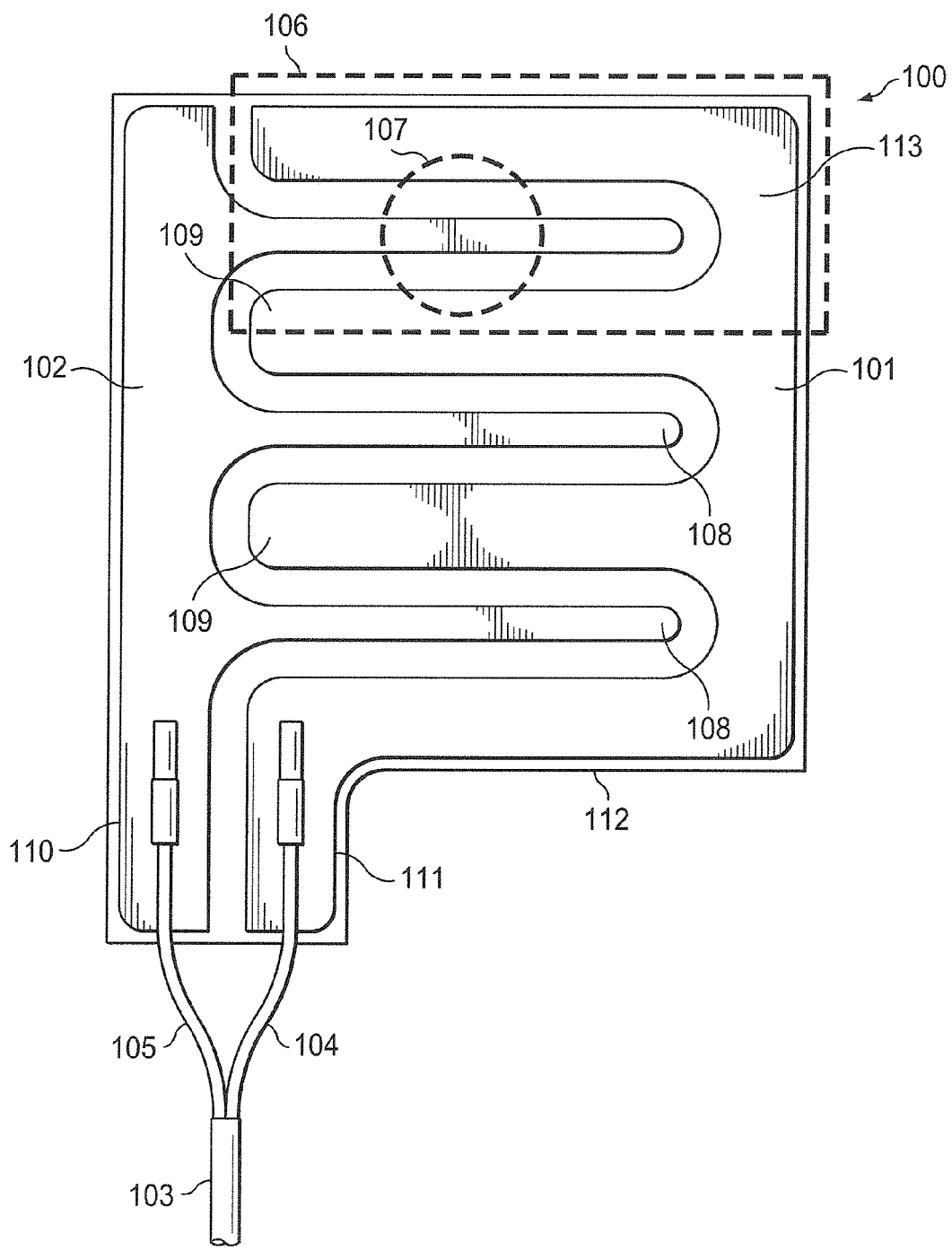
FIG. 1 is an illustration of a neurostimulation device having opposed, interleaved arms according to an example embodiment.

An example embodiment is illustrated in FIG. 1. This embodiment provides an array of physical electrodes with alternating polarity electrodes whose spacing is held at a uniform distance. The distance is preferably less than about 0.75 inches and, even more preferably, less than about 0.40 inches. The ratio of the area of a treating electrode relative to the surrounding opposite polarity electrode is preferably at least about 1.2/1. The array of electrodes "self-selects" the optimal treatment electrodes at the preferred treatment location via Ohm's law since the greatest energy is delivered under the electrode located on the lowest impedance points. Further, the array self-directs energy to the most advantageous area, or electrode node within an array of nodes. Therefore, both scanning and treatment is performed automatically and concurrently.

FIG. 1 illustrates a neurostimulation device 100. Device 100 comprises a plurality of conductive plates. The illustrated device has a first conductive plate 101 and a second conductive plate 102. First and second conductive plates 101, 102 may be viewed as first and second physical electrode elements. Alternate configurations may have more than two plates, particularly if additional electrical leads were incorporated. In certain embodiments, an electrode configuration is provided in which there are more virtual electrodes pairs, or nodes, than there are physical electrode elements.

An electrical lead pair 103 is connected at one end to a power source (not shown). The electrical lead pair 103 splits into a first electrical lead 104 and a second electrical lead 105. First electrical lead 104 is coupled to first conductive plate 101 at first lead base 111 of first conductive plate 101. Second electrical lead 105 is coupled to second conductive plate 102 at second lead base 110 of second conductive plate 102. First conductive plate 101 comprises a plurality of first fingers 109 and second conductive plate 102 comprises a plurality of second fingers 108. It should be understood that the electrical leads may be reversed to reverse the polarity of the virtual electrode pairs.

First and second conductive plates 101 and 102 may be formed from any suitable material. Preferably the material is highly conductive, such as, for example, gold, silver, stainless steel, copper, or hydrogel. In one embodiment, the conductive plates 101, 102 are attached to a base or backing pad 112, which may comprise any suitable insulating material such as, for example, polyethylene foam, or kapton. In one embodiment a self-adhering, flexible laminate is used, which, on the side opposite the conductive plates, adheres to skin without the need for additional attachment methods such as straps. Preferably, the conductive material itself is self-adhering such as sticky, conductive hydrogel.

Preferably, first electrical lead 104 is a higher voltage lead and second electrical lead 105 is a return, lower voltage lead. Thus, first conductive plate 101 and first fingers 109 are higher voltage. Likewise, second conductive plate and second fingers 108 are lower voltage. Also, it is preferred that first fingers 109 are wider than second fingers 108. Stated another way, fingers 109 are wide or thick, while fingers 108 are narrow or thin. The width or thickness of fingers 109, 108 depends on the desired ratio of the lower voltage electrode surface to the higher voltage electrode surface, as well as the desired spacing between electrodes. It should be understood that the relative voltage potential of the respective conductive plates may be reversed.

First and second fingers 109, 108 interlace to form a plurality of virtual electrodes. One such virtual electrode is illustrated by dashed box 106. A virtual electrode includes a thin second finger 108 and a portion of each of two thick first fingers 109. The virtual electrode can also be viewed as including the bridge portion 113 between the two portions of the first fingers 109. Thus, the portions of the first fingers 109, together with the bridge portion 113, form a higher voltage electrode and the thin finger 108 between the two thick finger portions forms the lower voltage electrode. Area 107 represents a stimulation node, as will be described elsewhere herein.

In an alternate embodiment, instead of using "self-selecting" physical pairs of electrodes (i.e. electrodes that provide self-selecting stimulation), a "self-directing stimulation electrode" is provided. Such an electrode creates a "self-directing stimulation node" without the need for individual physical electrodes when certain characteristics are maintained. "Self-selecting" refers to the ability of the device to "create" a plurality of virtual electrodes. This is due to the relationship of the combination of the area ratio and spacing of the physical electrodes. Even if the tissue is healthy and uniform, the device will still create or "self-select" virtual electrodes. "Self-directing" means that the embodiment directs more energy to those virtual electrodes which are the preferred ones to treat. It "self-directs" to the subset of virtual electrodes which have the lower relative impedance.

By maintaining a relatively high area ratio and close spacing, the energy is naturally concentrated at the points of low impedance via Ohm's law effectively creating "self-directed stimulation nodes" along the circuitous conductor path without the need to have individual physical electrodes. Thus, this design "self-selects" areas to become virtual treatment nodes and also directs the energy density to those nodes with lowest relative impedance. Preferably, the spacing between the electrodes is less than about 0.40 inches. Even more preferably the spacing is about 0.25 and the ratio of the relative areas of the electrodes is between about 1.20:1 and 5.0:1. Close spacing provides the ability to deliver high energy to treatment points without causing painful muscle contraction. Higher energy density is needed in order to stimulate the cutaneous nerve fibers. So, if the amount of energy that can be delivered is limited by painful muscle contractions, then the treatment effectiveness will be reduced. The concentrated energy relocates along the circuitous conductive path as the impedance value varies on the treated skin. This dynamic feature provides concentrated stimulation to the most preferred areas on the skin during an unattended treatment period, thereby automatically scanning and treating without the need for complex computer algorithms and human intervention.

In at least one embodiment, a self-adhering, flexible laminate is used as a backing or support for the electrode array. The laminate adheres to the skin without the need for additional attachment methods such as straps. This enables the self-directing stimulation electrode to be used on curved and concave human body parts such as a shoulder or lower back. An additional benefit of such a self-directing stimulation electrode is that it is not limited in dimensions. For example, one can treat an entire back via the use of a single self-directing stimulation electrode.

Other aspects of the various embodiments are as follows. As shown, for example, in FIG. 1, there are two physical electrodes. However, due to the configuration of the electrodes, including their shapes and relative positioning, a plurality of electrode nodes, or virtual electrode pairs, are created. One such electrode node is indicated in FIG. 1 in the region indicated by dashed area 107. It can be seen that there are additional electrode nodes, or virtual electrode pairs, created by the serpentine shape, and relative positioning, of the two physical electrodes. One advantage of this approach, in addition to those mentioned elsewhere in this disclosure, is that the number of electrical connections needed for the apparatus is reduced. Normally, in an array of physical electrode elements, there would be two electrical connections for every pair. In the embodiment illustrated, for example, in FIG. 1, only two physical electrical connections (e.g., higher voltage and lower voltage) are needed even though there are more than one pair of electrode nodes, or virtual electrode pairs. Other shapes and configurations described herein provide different numbers and arrangements of the electrode nodes or virtual electrode pairs. This is accomplished while maintaining just two physical electrode elements and, therefore, only two necessary electrical connections.

Preferably the device is driven by a constant current source. This will, among other things, prevent burning and discomfort that could occur if a typical transcutaneous electrical nerve stimulation (TENS)-type approach is used. From a therapeutic perspective it is important to achieve high density current to achieve superior clinical results, particularly in post-operative applications. This is achieved with the self-directing stimulation electrode by virtue of the relative size and spacing of the configuration which maintains a superficial delivery of the stimulation, thus avoiding the inhibiting effects and painful sensations of muscle contraction.

Figure 2:
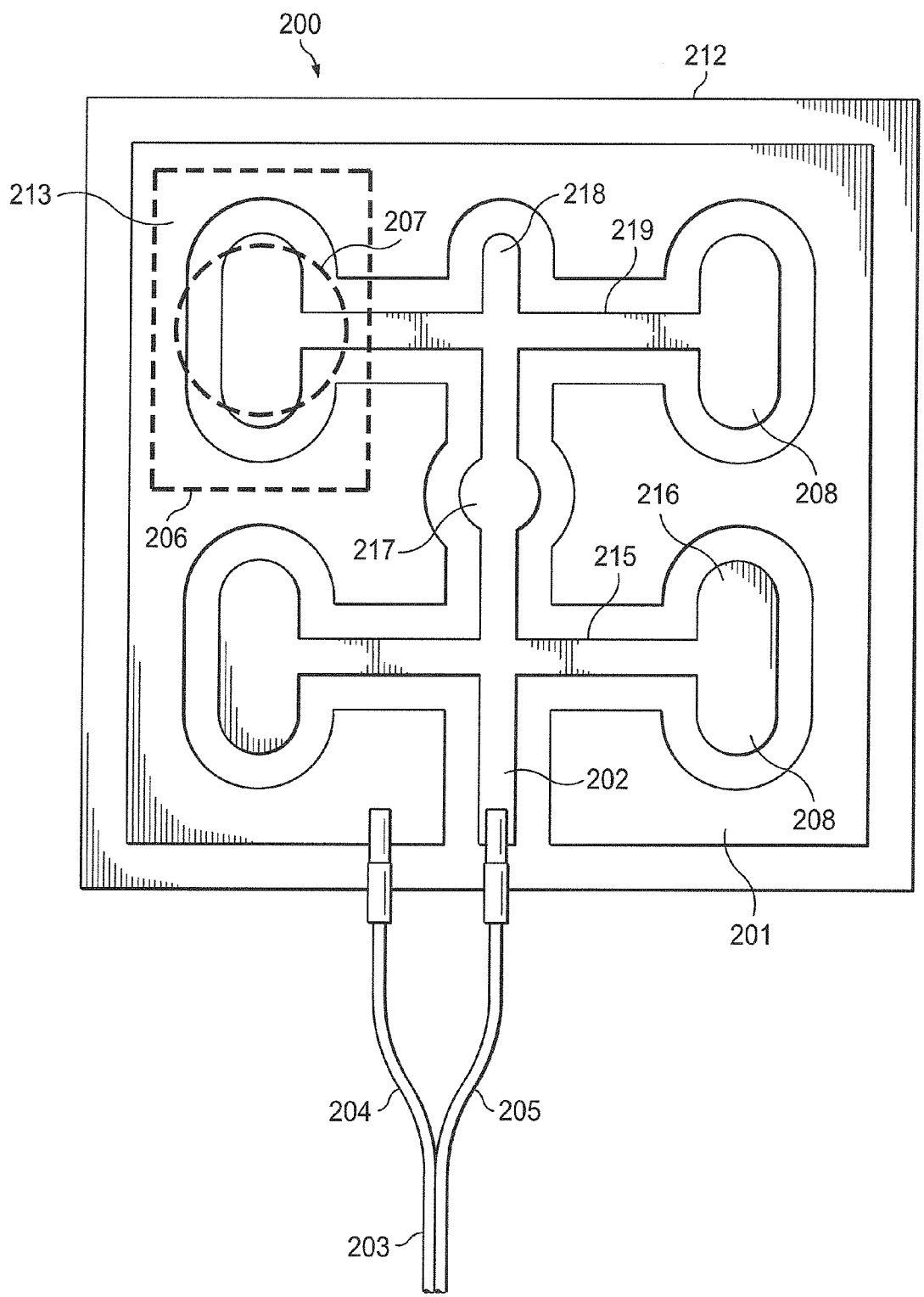
FIG. 2 is an illustration of an alternate embodiment of a neurostimulation device having cross structures and T-shaped arms according to an example embodiment.

FIG. 2 illustrates an alternate configuration of virtual electrode pairs provided by using two physical electrode elements. Device 200 has a backing 212 on which are attached a first physical electrode element 201 and a second physical electrode element 202. Second physical electrode element 202 has a longitudinal member 218 and a pair of transverse members 219. Members 218 and 219 form a pair of cross structures. Each cross structure has a pair of arms 215. Each arm 215 ends in a longitudinal pad 216. Arm 215 and pad 216 form a T-shaped conductive element. Thus, second physical electrode element 202 comprises a plurality of fingers 208, each finger comprising an arm 215 and a pad 216. An additional treatment pad 217 may be included as a supplemental node. Pad 217 separates the two cross elements formed by first physical electrode element 201. Also, it should be understood, that additional cross elements, in both the longitudinal and transverse directions, may be formed by first physical electrode element 201. Thus, the array of virtual electrode pairs may include more pairs than the four that are illustrated.

First physical electrode element 201 comprises a plate that surrounds second electrode element 202 while maintaining a relatively constant spacing between the two physical electrode elements. It can be seen that the configuration of first and second physical electrode elements 201, 202 provides an array of electrode nodes or virtual electrode pairs. One such virtual electrode pair exists in the area indicated by the dashed box 206 and its corresponding electrode node is indicated by the area of dashed circle 207. Virtual electrode pair 206 comprises an pad 216, a portion of arm 215, and a C-shaped portion of first physical electrode element 201 that partially surrounds pad 216. It should be noted that the precise extent of the physical elements that comprise a virtual electrode pair is not exact and a virtual electrode pair may be viewed as including more or less than the physical portions indicated by dashed box 206.

As already noted, additional virtual electrode pairs may be provided in the transverse direction. In this case, all but the outermost virtual electrode pair will have a negative portion that comprises two opposed cup-shaped portions of the first physical electrode element.

In the illustrated configuration, first physical electrode element 201 is coupled to a higher voltage electrical lead 204 and second physical electrode element 202 is coupled to lower voltage electrical lead 205. Connections 204 and 205 collectively form electrical lead pair 203, which is coupled to a power source (not shown). Preferably, the configuration illustrated provides virtual electrodes wherein with area ratios and relative spacing as previously described. However, the relative areas of the positive and negative electrode surfaces, as well as the spacing between electrode elements, may be changed to achieve different desired results. Further, it should be understood that in this embodiment, and in other embodiments described herein, the polarity of the physical electrode elements may be reversed.

Figure 3:
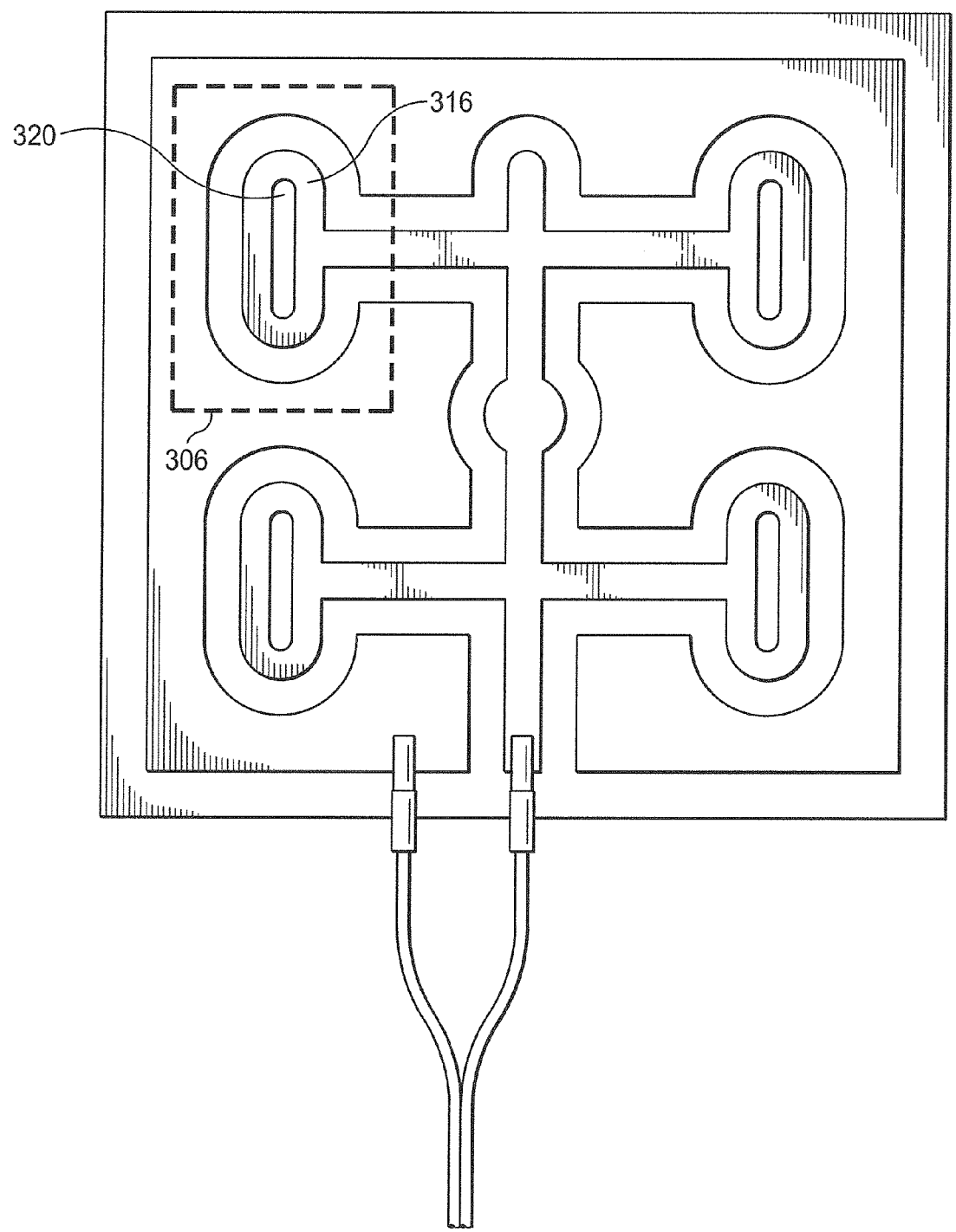
FIG. 3 is an illustration of an alternate embodiment of a neurostimulation device having cross structures and T-shaped arms with central voids according to an example embodiment.

FIG. 3 illustrates another alternate embodiment. This example embodiment is similar to that described in connection with FIG. 2. However, in this example, the pads 316 have voids 320 formed therein. This creates ring-shaped pads 316. Preferably, the spacing provided by a void 320 (e.g., from one inward edge of the ring-shaped pad transversely to the opposite edge) is the same as the other spacing between the two respective physical electrode elements. However, this is not required. This illustrated configuration results in a plurality of virtual electrode nodes or virtual electrode pairs, an example of which is indicated generally by the area within the dashed box 306.

Voids 320 and the resulting ring-shaped pads 316 result in a configuration that allows further modification of the area ratios without changing the electrode spacing.

Figure 4:
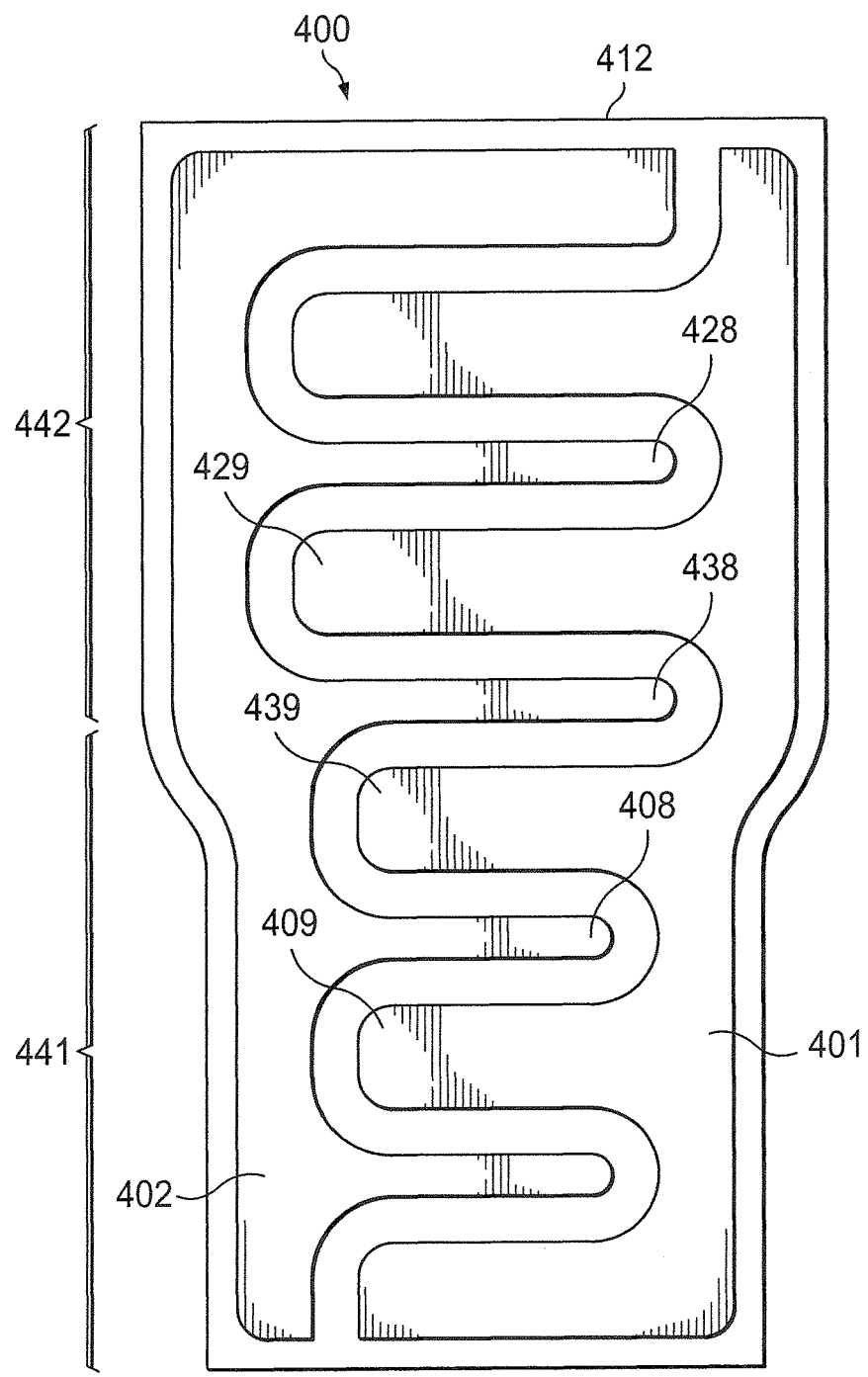
FIG. 4 is an illustration of an alternate embodiment of a neurostimulation device having opposed interleaved arms and multiple electrode array regions according to an example embodiment.

FIG. 4 illustrates yet another example embodiment. Device 400 comprises first physical electrode element 401 and second physical electrode element 402 disposed on a backing 412. The two physical electrode elements have fingers that are interleaved to create virtual electrode pairs or nodes. In this regard, this embodiment is similar to the embodiment illustrated in FIG. 1, for example.

Device 400, however, has a plurality of array portions that are shaped to adapt to a predetermined treatment region. In this embodiment, for example, the shape may correspond to a human's back. Thus, one part of device 400 may correspond to an upper back region, while another part of device 400 may correspond to a lower back region. The application of device 400 to a human back region is an example only, and it should be understood that the device may have different combinations of electrode array areas to correspond to different shapes of overall treatment areas, such as would be found, for example, at different parts of a human body.

In the illustrated example, device 400 has a first portion 441 and a second portion 442. Portion 442 has a larger overall surface area than first portion 441. The larger portion 442 may be utilized, for example, to correspond to a larger treatment region such as the upper back, while the smaller portion 441 may be used to treat a smaller area such as the lower back. Thus, device 400 may be used to simultaneously treat to differently shaped treatment areas, such as two different parts of the human body, for example.

First portion 442 has a plurality of opposed, interleaved protrusions, or fingers, provided by the two physical electrode elements 401, 402. As with certain other example embodiments described herein, the fingers can be viewed has having parallel, longitudinal axes in a transverse direction of the respective device. First physical electrode element 401 has first protrusions 409 and second physical electrode element 402 has second protrusions 408. The interleaved fingers provide a plurality of virtual electrode pairs or nodes as previously described.

Second portion 442 also comprises a plurality of opposed, interleaved, parallel, transverse protrusions, or fingers 428, 429. These fingers similarly create a plurality of virtual electrode pairs, or nodes, as previously described. It can be seen that the respective fingers 428, 429 are longer than the fingers 408, 409 of first portion 441. Thus, the virtual electrode pairs of second portion 442 have larger overall surface areas as compared with the virtual electrode pairs of first portion 441. There is also a transition area between first portion 441 and second portion 442. In this example, the transition area comprises a first transition protrusion 438 and a second transition protrusion 439. Protrusions 438 and 439 are opposed, parallel, transverse, and interleaved as is the case with the other protrusions of device 400. However, it can be seen that each of respective first and second transition protrusions 438, 439 has a long edge and a short edge. The short edge of second transition protrusion 439 corresponds to the length of the protrusions of first portion 441. The long edge of first transition protrusion 438 corresponds to the length of the protrusions of second portion 442. The short edge of first transition protrusion 438 corresponds to the long edge of second transition protrusion 439. In this way, the geometry of the transition portion provides a stepped area to provide a transition from a relatively smaller electrode array area to a relatively larger electrode array area. It should be understood that the concept of transition areas and differently-sized array portions of a device may be applied to devices having different configurations than that shown in FIG. 4. For instance, the size of the virtual electrode pairs may be continuously variable down to the length of the treatment area. In other words, the transition does not have to be a step function.

Figure 5:
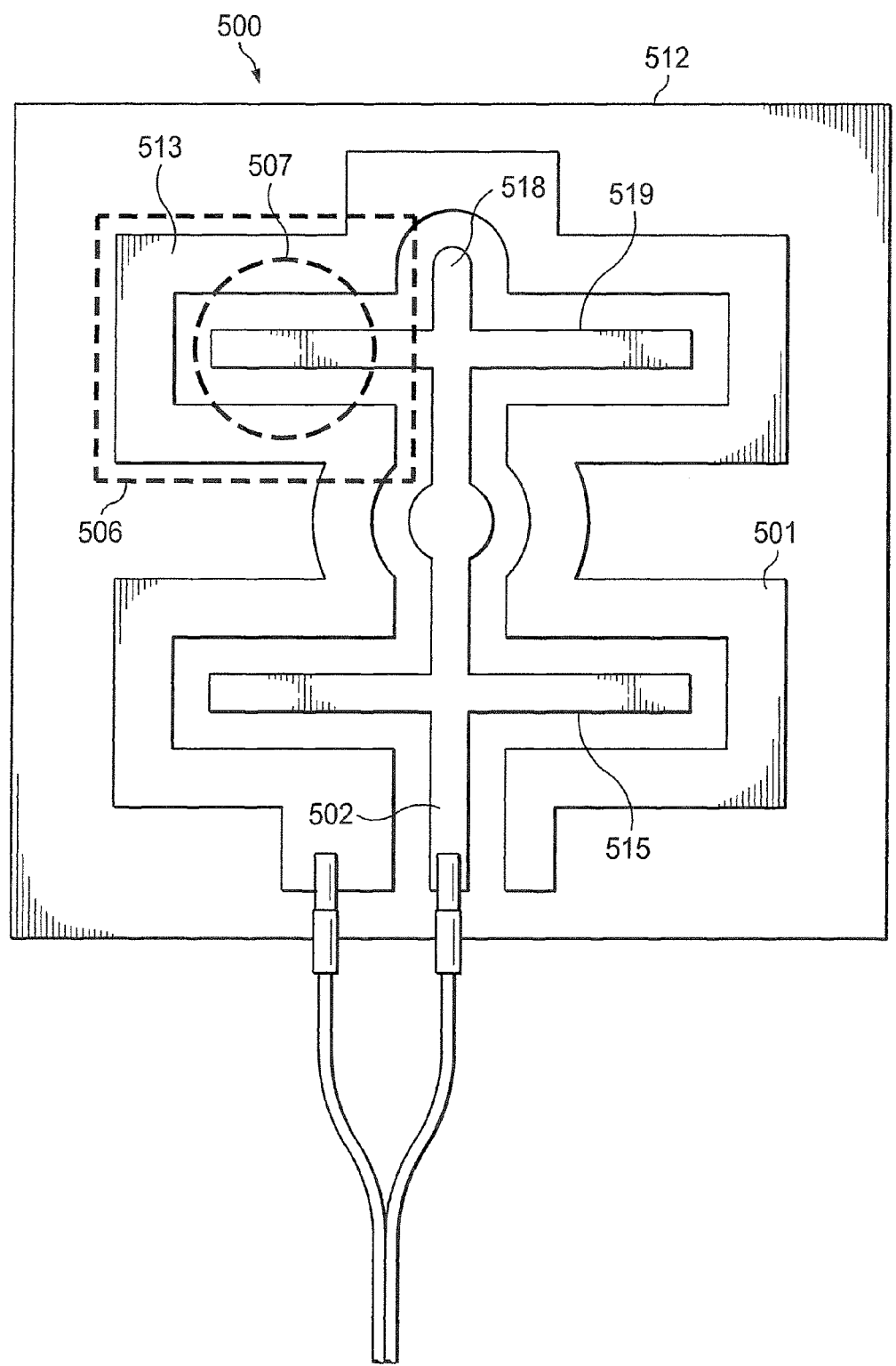
FIG. 5 is an illustration of an alternate embodiment of a neurostimulation device having cross structures according to an example embodiment.

FIG. 5 illustrates yet another example embodiment. Device 500 comprises a first physical electrode element 501 and a second physical electrode element 502. First and second physical electrode elements 501, 502 are disposed on backing 512 and coupled to electrical leads as previously described. First and second physical electrode elements 501, 502 cooperate to provide a plurality of transverse virtual electrode pairs or nodes.

Second physical electrode element 502 comprises a longitudinal element 518 and two transverse elements 519. Each transverse element 519 comprises a pair of arms 515 that extend transversely and outwardly from longitudinal element 518. Thus, there are two pairs of opposing transverse arms 515. The configuration of second physical electrode element 502 thereby forms a pair of cross structures.

First physical electrode element 501 comprises a structure which surrounds second physical electrode element 502. Preferably the relative area ratios and the spacing between first and second physical electrode elements 501 and 502 is as previously described in connection with certain other example embodiments. Portions of first and second physical electrode elements 501, 502 form virtual electrode pairs or nodes. One example virtual electrode pair is generally indicated by the dashed box 506. The corresponding virtual electrode node is indicated by dashed circle 507. Such a virtual electrode pair comprises an arm 515 and a portion 513 of first physical electrode element 501, which partially surrounds arm 515. The portion 513 is illustrated as a C-shaped portion.

Figure 6:
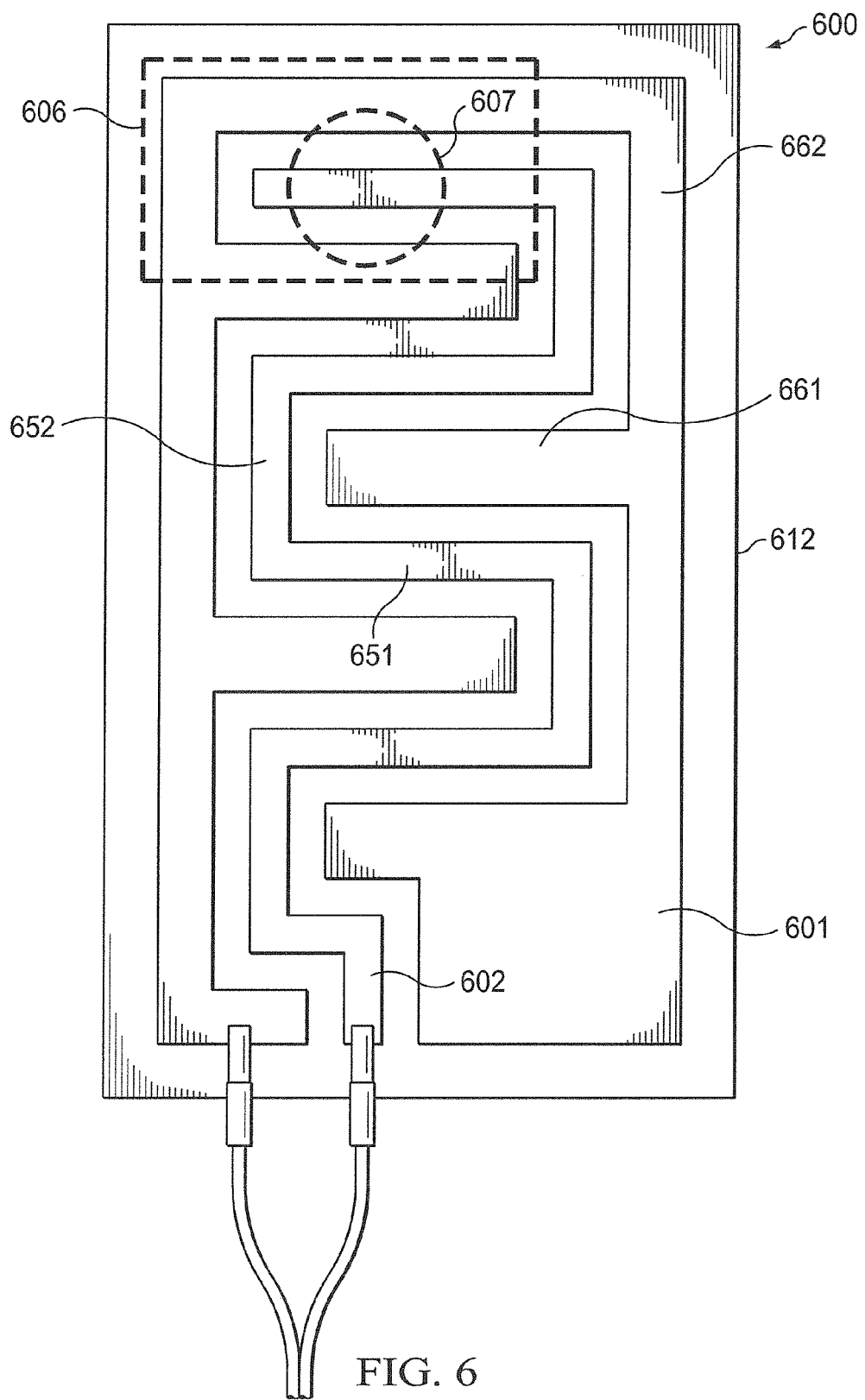
FIG. 6 an illustration of an alternate embodiment of a neurostimulation device having a serpentine element according to an example embodiment.

FIG. 6 illustrates yet another example embodiment. Device 600 comprises first physical electrode element 601 and second physical electrode element 602. First and second physical electrode elements 601, 602 are disposed on backing 612 and coupled to electrical leads as previously described. First and second physical electrode elements 601, 602 cooperate to provide a plurality of transverse virtual electrode pairs or nodes.

Second physical electrode element 602 comprises a serpentine element 518 that provides a plurality of second transverse, parallel arms 651. The second arms 651 are joined at alternating ends by longitudinal second joining sections 652. As illustrated, one arm 651 adjacent the electrical leads is shorter than the other arms 651. Although five arms are illustrated, there may exist more or fewer than five arms.

First physical electrode element 601 comprises a structure which surrounds second physical electrode element 602. Preferably the relative area ratios and the spacing between first and second physical electrode elements 601 and 602 is as previously described in connection with certain other example embodiments. First physical electrode element 601 provides a plurality of first alternating, opposed, transverse arms 661, which are joined by first joining sections 662.

Portions of first and second physical electrode elements 601, 602 form virtual electrode pairs or nodes. One example virtual electrode pair is generally indicated by the dashed box 606. The corresponding virtual electrode node is indicated by dashed circle 607. Such a virtual electrode pair comprises a first arm 651 and a portion of first physical electrode element

601, which partially surrounds arm 651. The portion of first physical electrode element 601 comprises at least a portion each of two arms 661 and a first joining section 662. It should be understood that at the end of the device opposite the electrical connections, the "arm" 661 extends all the way across the device and does not have a terminus as do the other arms 661. The portion of first physical electrode element 601 which forms part of a given virtual electrode may be viewed as a C-shaped portion.

It should be understood that the various figures and their description illustrate example embodiments of the apparatus and various aspects of the apparatus may be added, eliminated, and/or substituted for those shown. Such modifications may be made as is desired, suitable, and/or advantageous for performing the functionality described herein. Such modifications are within the scope of the invention. For example, it should be understood that one or both of the first and second physical electrode elements of various embodiments may be split or separated into two or more components. Each component may be provided with appropriate electrical leads such that the appropriate polarity of the components is achieved. Preferably, even if one or more physical electrode elements is separated into two or more components, the first physical components and second physical components cooperate to provide a number of virtual electrode pairs that is greater than the number of first or second physical components.

Numerous other changes, substitutions, variations, alterations, and modifications may be ascertained by those skilled in the art and it is intended that the present invention encompass all such changes, substitutions, variations, alterations and modifications as falling within the spirit and scope of this description.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus for providing neurostimulation, comprising:
   a first physical electrode element having a first polarity; and
   a second physical electrode element having a second polarity different from the first polarity;
   the first and second physical electrode elements cooperating to form a plurality of virtual electrode pairs, wherein each pair comprises a first electrode part and a second part, the first electrode part comprising a portion of the first physical electrode element and the second electrode part comprising a portion of the second physical electrode element,
   wherein a relative are ratio between the first and second electrode parts is between about 1.2:1 and about 5.0:1.

2. The apparatus of claim 1, wherein a distance between the first and second electrode parts is less than about 0.40 inches.

3. The apparatus of claim 1, wherein at least one of the first electrode parts comprises an arm, and wherein at least one of the second electrode parts comprises a C-shaped portion of the first physical electrode element, the C-shaped portion at least partially surrounding the arm.

4. The apparatus of claim 1, wherein at least one of the first electrode parts comprises a T-shaped portion, the T-shaped portion comprising an arm and a pad extending from the arm, and wherein at least one of the second electrode parts composes a C-shaped portion of the first physical electrode element, the C-shaped portion at least partially surrounding the T-shaped portion.

5. The apparatus of claim 1, wherein the second physical electrode element comprise a longitudinal element and at least two transverse elements crossing the longitudinal element to form at least two cross structures, wherein each of the cross structures comprises at least two of the arms of the plurality of virtual electrode pairs.

6. The apparatus of claim 1, wherein the first physical electrode element comprises a first base portion from which extend a plurality of first arms, and wherein the second physical electrode element comprises a second base portion from which extend a plurality of second arms, the first and second arms interleaved and opposed to form the plurality of virtual electrode pairs.

7. The apparatus of claim 6, wherein alternating ones of the arms of the plurality of virtual electrode pairs extend transversely in opposite directions.

8. The apparatus of claim 1, wherein the second physical electrode element comprises a serpentine element having a plurality of transverse arms, at least one of the transverse arms of the serpentine element comprising an arm of at least one of the virtual electrode pairs.

9. The apparatus of claim 1, further comprising first and second electrical leads coupled at one end to the respective first and second physical electrode elements, the other end of the electrical leads operable to be coupled to a power source, wherein, when power is applied to the electrical leads, at least one virtual electrode pair provides a virtual electrode node.

10. The apparatus of claim 1, wherein at least one of the first and second physical electrode elements comprises a plurality of distinct and separate components, and wherein the number of virtual electrode pairs is greater than either the number of components of the first physical electrode element or the number of components of the second physical electrode element.

11. The apparatus of claim 1, wherein the distance between the first and second electrode parts is a predetermined spacing, and wherein a relative area ratio between the first and second electrode parts is a predetermined ratio, and further wherein the predetermined spacing and predetermined ratio are selected to enable the apparatus to self-direct treatment energy to one or more virtual electrode pairs.

12. An apparatus for providing neurostimulation, comprising:
    a first physical electrode element having a first polarity and a second physical electrode element having a second polarity different from the first polarity;
    the first and second physical electrode elements cooperating to form a plurality of virtual electrode pairs, wherein each pair comprises a first electrode part and a second electrode part, the first electrode part comprising a portion of the first physical electrode element and the second electrode part comprising a portion of the second physical electrode element,
    wherein the distance between the first and second electrode parts is a predetermined spacing, and wherein a relative area ratio between the first and second electrode parts is a predetermined ratio, and further wherein the predetermined spacing and predetermined ratio are selected to enable the apparatus to self-direct treatment energy to one or more virtual electrode pairs.

13. The apparatus of claim 12, wherein a distance between the first and second electrode parts is less than about 0.40 inches.

14. The apparatus of claim 12, wherein a relative area ratio between the first and second electrode parts is between about 1.2:1 and about 5.0:1.

15. The apparatus of claim 12, wherein at least one of the first electrode parts comprises an arm, and wherein at least one of the second electrode parts comprises a C-shaped portion of the first physical electrode element, the C-shaped portion at least partially surrounding the arm.

16. The apparatus of claim 12, wherein at least one of the first electrode parts comprises a T-shaped portion, the T-shaped portion comprising an arm and a pad extending from the arm, and wherein at least one of the second electrode parts comprises a C-shaped portion of the first physical electrode element, the C-shaped portion at least partially surrounding the T-shaped portion.

17. The apparatus of claim 12, wherein the second physical electrode element comprises a longitudinal element and at least two transverse elements crossing the longitudinal element to form at least two cross structures, wherein each of the cross structures comprises at least two of the arms of the plurality of virtual electrode pairs.

18. The apparatus of claim 12, wherein the first physical electrode element comprises a first base portion from which extend a plurality of first arms, and wherein the second physical electrode element comprises a second base portion from which extend a plurality of second arms, the first and second arms interleaved and opposed to form the plurality of virtual electrode pairs.

19. The apparatus of claim 18, wherein alternating ones of the arms or the plurality of virtual electrode pairs extend transversely in opposite directions.

20. The apparatus of claim 12, wherein the second physical electrode element comprises a serpentine element having a plurality of transverse arms, at least one of the transverse arms of the serpentine element comprising an arm of at least one of the virtual electrode pairs.

21. The apparatus of claim 12, further comprising first and second electrical leads coupled at one end to the respective first and second physical electrode elements, the other end of the electrical leads operable to be coupled to a power source, wherein, when power is applied to the electrical leads, at least one virtual electrode pair provides a virtual electrode node.

22. The apparatus of claim 12, wherein at least one of the first and second physical electrode elements comprises a plurality of distinct an separate components, and wherein the number of virtual electrode pairs is greater than either the number of components of the first physical electrode element or the number of components of the second physical electrode element.

\* \* \* \* \*